(12) United States Patent
Kearney et al.

(10) Patent No.: US 11,479,583 B2
(45) Date of Patent: Oct. 25, 2022

(54) TARGETED MOSQUITOCIDAL TOXINS

(71) Applicant: BAYLOR UNIVERSITY, Waco, TX (US)

(72) Inventors: Christopher Michel Kearney, Waco, TX (US); Grace Pruett, Waco, TX (US)

(73) Assignee: BAYLOR UNIVERSITY, Waco, TX (US)

( * ) Notice: Subject to any disclaimer, the term of this patent is extended or adjusted under 35 U.S.C. 154(b) by 446 days.

(21) Appl. No.: 15/944,285

(22) Filed: Apr. 3, 2018

(65) Prior Publication Data

US 2018/0282757 A1 Oct. 4, 2018

Related U.S. Application Data

(60) Provisional application No. 62/481,199, filed on Apr. 4, 2017.

(51) Int. Cl.
| | |
|---|---|
| *C07K 14/18* | (2006.01) |
| *C12N 15/82* | (2006.01) |
| *C07K 14/435* | (2006.01) |
| *C07K 14/005* | (2006.01) |
| *A01N 63/50* | (2020.01) |

(52) U.S. Cl.
CPC .......... *C07K 14/1825* (2013.01); *A01N 63/50* (2020.01); *C07K 14/005* (2013.01); *C07K 14/43518* (2013.01); *C12N 15/8242* (2013.01); *C12N 15/8286* (2013.01); *C07K 2319/00* (2013.01); *C07K 2319/55* (2013.01); *C12N 2770/24122* (2013.01)

(58) Field of Classification Search
None
See application file for complete search history.

(56) References Cited

U.S. PATENT DOCUMENTS

| | | | |
|---|---|---|---|
| 5,674,846 | A | 10/1997 | Johnson et al. |
| 5,770,192 | A | 6/1998 | Cayley et al. |
| 6,583,264 | B2 | 6/2003 | King et al. |
| 7,173,106 | B2 | 2/2007 | King et al. |
| 7,279,547 | B2 | 10/2007 | King et al. |
| 7,354,993 | B2 | 4/2008 | King et al. |
| 7,575,758 | B2 | 8/2009 | King et al. |
| 8,217,003 | B2 | 7/2012 | Tedford et al. |
| 8,293,868 | B2 | 10/2012 | King et al. |
| 8,334,366 | B1 | 12/2012 | Hughes et al. |
| 8,362,201 | B2 | 1/2013 | King et al. |
| 8,501,684 | B2 | 8/2013 | Tedford et al. |
| 8,703,910 | B2 | 4/2014 | Tedford et al. |
| 9,352,022 | B2 | 5/2016 | Tedford et al. |
| 9,388,428 | B2 | 7/2016 | Nasar et al. |
| 9,567,381 | B2 | 2/2017 | Kennedy et al. |
| 9,957,524 | B2 | 5/2018 | Bowen et al. |
| 10,117,433 | B2 | 11/2018 | Gatehouse et al. |
| 10,669,319 | B2 | 6/2020 | Kennedy et al. |
| 10,881,712 | B2 | 1/2021 | King et al. |
| 2002/0064543 | A1 | 5/2002 | King et al. |
| 2003/0199039 | A1 | 10/2003 | King et al. |
| 2004/0138423 | A1 | 7/2004 | King et al. |
| 2006/0242734 | A1 | 10/2006 | King et al. |
| 2007/0066529 | A1* | 3/2007 | King et al. ............. A01N 65/00 514/12 |
| 2008/0260789 | A1 | 10/2008 | King et al. |
| 2008/0300210 | A1 | 12/2008 | German et al. |
| 2009/0023183 | A1 | 1/2009 | Oh et al. |
| 2009/0183282 | A1 | 7/2009 | King et al. |
| 2010/0081619 | A1 | 4/2010 | Tedford et al. |
| 2011/0237502 | A1 | 9/2011 | King et al. |
| 2011/0239331 | A1 | 9/2011 | King et al. |
| 2013/0017992 | A1 | 1/2013 | Tedford et al. |
| 2013/0097729 | A1 | 4/2013 | Bonning et al. |
| 2013/0097731 | A1 | 4/2013 | Avisar et al. |
| 2013/0184434 | A1 | 7/2013 | Tedford et al. |
| 2013/0276155 | A1 | 10/2013 | King et al. |
| 2014/0187478 | A1 | 7/2014 | Tedford et al. |
| 2014/0227765 | A1 | 8/2014 | Nasar et al. |
| 2014/0366227 | A1 | 12/2014 | Gatehouse et al. |
| 2015/0148288 | A1 | 5/2015 | Kennedy et al. |
| 2015/0274786 | A1 | 10/2015 | Bowen et al. |
| 2016/0227766 | A1 | 8/2016 | Tedford et al. |
| 2016/0311867 | A1 | 10/2016 | Fitches et al. |
| 2017/0174731 | A1 | 6/2017 | Kennedy et al. |

(Continued)

FOREIGN PATENT DOCUMENTS

| | | |
|---|---|---|
| WO | 2010/077672 | 7/2010 |
| WO | 2012/131302 | 10/2012 |

OTHER PUBLICATIONS

Hung et al (J. Virol., 2004, 78(1): 378-388).*
Poopathi et al (Journal of Physiology and Pathophysiology, 2010, 1(3): 22-38).*
Nakasu et al (Proc. Biol. Sci., 2014, 281(1787): Jun. 19, 2014).*
Erb et al (Virology, 2010, 406: 328-335).*
Bende (2015, Bioinsecticides for the control of human disease vectors. PhD Thesis, Institute for Molecular Bioscience, The University of Queensland, https://doi.org/10.14264/uql.2015.645).*

(Continued)

*Primary Examiner* — Stephen Uyeno
(74) *Attorney, Agent, or Firm* — Jackson Walker LLP

(57) ABSTRACT

Insecticidal toxins described herein are fused toxin peptides made up of a targeting domain fused to a toxin domain. The targeting peptide generates a specific association with mosquitoes by causing the fused toxin peptide to bind mosquitoes in a way that leads to the insecticidal activity. Transgenic plants described herein are mosquitocidal by expressing an insecticidal toxin protein in nectar that includes a targeting peptide to ensure specificity against mosquitoes. These transgenic plants serve as role models for safety, since they are non-crop plants and specific to one mosquito species.

11 Claims, 8 Drawing Sheets

Specification includes a Sequence Listing.

(56) References Cited

U.S. PATENT DOCUMENTS

| | | | |
|---|---|---|---|
| 2018/0186846 | A9 | 7/2018 | Kennedy et al. |
| 2018/0282757 | A1 | 10/2018 | Kearney et al. |
| 2018/0362598 | A1 | 12/2018 | Carlson et al. |
| 2019/0119336 | A1 | 4/2019 | Fitches et al. |
| 2019/0239513 | A1 | 8/2019 | Bonning et al. |
| 2019/0261634 | A1 | 8/2019 | Carlson et al. |
| 2020/0060284 | A1 | 2/2020 | Hahne et al. |
| 2020/0061156 | A1 | 2/2020 | King et al. |
| 2020/0207818 | A1 | 7/2020 | Schneider et al. |
| 2020/0255482 | A1 | 8/2020 | Kennedy et al. |
| 2020/0277345 | A1 | 9/2020 | Kennedy et al. |

OTHER PUBLICATIONS

Bonning, et al., "Toxin delivery by the coat protein of an aphid-vectored plant virus provides plant resistance to aphids", Nature Biotechnology, vol. 32, No. 1, Jan. 2014, 6 pages.

Chen, et al., "Nectar protein content and attractiveness to Aedes aegypti and Culex pipiens in plants with nectar/insect associations", Acta Tropica, 2015, www.elsevier.com/locate/actatropica, 8 pages.

Hrobowski, et al., "Peptide inhibitors of dengue virus and West Nile virus infectivity", BioMed Central—Virology Journal, Jun. 1, 2005, 2:49, 10 pages.

Hung, et al., "An External Loop Region of Domain III of Dengue Virus Type 2 Envelope Protein Is Involved in Serotype-Specific Binding to Mosquito but Not Mammalian Cells", Journal of Virology, Jan. 2004, vol. 78, No. 1, pp. 378-388, downloaded on Nov. 1, 2018 at http://jvi.asm.org.

Notification of Transmittal of the International Preliminary Report on Patentability dated Oct. 17, 2019 by the International Bureau of WIPO for International Application No. PCT/US2018/025907 containing the Written Opinion of the International Searching Authority—The European Patent Office; 10 pages.

Notification of Transmittal of the International Search Report and Written Opinion issued by the European Patent Office, for International Application No. PCT/US2018/025907, dated Jun. 28, 2018, 18 pages.

Pinson, Marisa, "Abstract—Evaluating and Isolating Promoters in Impatiens Walleriana: Towards the Development of Mosquitocidal Nectar", A Thesis Submitted to the Faculty of Baylor University In Partial Fulfillment of the Requirements for the Honors Program, Waco, Texas, May 2016, 43 pages, retrieved from the internet Jun. 6, 2018 https://baylor-ir.tdl.org/baylor-ir/bitstream/handle/2104/9759/Pinson%20Honors%20Thesis%20BEARdocs.pdf?sequence=3&isAllowed=y.

Kim, et al., "Cholera toxin B subunit-domain III of dengue virus envelope glycoprotein E fusion protein production in transgenic plants", Protein Expression and Purification 74 (2010), pp. 236-241.

* cited by examiner

SEQUENCE LISTING

```
<160> NUMBER OF SEQ ID NOS: 3

<210> SEQ ID NO 1
<211> LENGTH: 16
<212> TYPE: PRT
<213> ORGANISM: Dengue virus

<400> SEQUENCE: 1

Met Ile Gly Val Glu Pro Gly Gln Leu Lys Leu Asn Trp Phe Lys Lys
1               5                   10                  15

<210> SEQ ID NO 2
<211> LENGTH: 37
<212> TYPE: PRT
<213> ORGANISM: Atrax robustus

<400> SEQUENCE: 2

Ser Pro Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30

Val Lys Arg Cys Asp
        35

<210> SEQ ID NO 3
<211> LENGTH: 9
<212> TYPE: PRT
<213> ORGANISM: Artificial Sequence
<220> FEATURE:
<223> OTHER INFORMATION: Linker

<400> SEQUENCE: 3

Gly Gly Ser Gly Gly Gly Ser Gly Gly
1               5
```

TARGETED MOSQUITOCIDAL TOXINS

This application claims priority to U.S. Provisional Patent Application No. 62/481,199, entitled "Targeted Mosquitocidal Toxins," filed Apr. 4, 2017, the entire contents of which are hereby incorporated by reference.

BACKGROUND

The present disclosure relates to a targeted mosquitocidal toxin and to plants engineered to produce a mosquitocidal toxin for control of mosquito populations.

Mosquitoes represent one of the most universally disliked pests. Aside from their common nuisance factor, they are carriers for a number of deadly and damaging illnesses. Mosquito-borne illnesses cause millions of deaths worldwide each year, particularly in developing countries. Vaccine development has been successful only with a certain proportion of viral diseases. These difficulties are compounded by the development of new pathogens with each passing decade, such as the current Zika and Chikungunya threats.

Efforts to control mosquito populations include local efforts aimed at removing standing water, as well as generalized and widespread insecticide spraying. These efforts have not shown great success, and in the case of insecticide spraying, have negative effects on non-target species. Pesticide programs have been the mainstay for mosquito control in the USA, but pesticides can have ecological consequences, as seen in massive honeybee kill of 2016 in South Carolina, from pesticide treatment in response to the Zika threat. Mosquito repellent is effective for limited situations, but, for everyday life especially for families, the discipline of daily application of repellent may break down. Even with the current mosquito control measures, many citizens of the USA simply stay indoors in the summer to avoid the risk of disease transmission, as well as the annoyance of mosquitoes.

SUMMARY

The present disclosure pertains to targeted insecticidal proteins that are toxic to mosquitoes but not to non-target insect species. The present disclosure also relates to plants engineered to produce the toxins. In particular embodiments, the transgenic plants express an insecticidal toxin protein that includes a targeting peptide to ensure specificity against mosquitoes. The insecticidal toxin may be produced in nectar made by the plants. These plants represent an ecologically sensitive, cost-effective and long-lived approach which leverages the mosquito population's critical requirement for nectar feeding.

Mosquito populations are critically dependent on nectar as a food source. Males use nectar and other sugar sources as their sole source of nutrition while females depend on it to energize their blood quest flights, for preparation for overwintering, and other purposes. Leveraging this fact, sugar baits dosed with pesticides have proven to be a viable control measure against mosquitoes. However, it would be preferable to avoid the use of pesticides altogether. Appropriate and effective delivery mechanisms for a mosquitocidal peptide would enable a biosafe mosquito control strategy.

Toxic peptides targeted to specific organisms have been produced. The specificity of antimicrobial peptides has been altered using targeting peptides and the fusions have been produced in high yield in *E. coli*. Chemically synthesized fusion peptides specifically toxic to *Staphylococcus aureus* and *Streptococcus mutans* have been produced. Further, transgenic plants expressing targeted fusion peptides were shown to be specifically resistant to *Fusarium* root rot fungus and aphids.

The present disclosure pertains to a targeted fusion peptide having a targeting peptide that is specific to mosquitoes and a toxin peptide that are fused together. The targeting peptide ensures that the fusion peptide is taken up, or bound in some fashion that induces toxicity of the toxin, by mosquitoes only. Unless the fusion peptide is taken up or bound in this fashion, the toxin peptide will lack toxicity. Accordingly, targeting the peptide to mosquitoes results in a toxin that has no effect against non-mosquito insects. The targeted fusion peptide may be expressed in any suitable organism, including yeast or *E. coli*, and then extracted, isolated, or purified for application as a mosquitocidal toxin.

In some embodiments, a plant is engineered to produce the targeted fusion peptide in a manner that will ensure that a mosquito imbibes, consumes, is exposed to or otherwise takes up the peptide. In some embodiments, a nectar plant is engineered to express the targeted fusion peptide in nectar. Nectar is a critical component of the mosquito life cycle and is highly attractive to them. Mosquito males depend upon nectar or a supplied sugar source for their survival while female mosquitoes require nectar to power their blood quest flights. Non-nectar plants may also be engineered to express the targeted fusion peptide, so long as it is expressed in a manner that permits mosquitoes to consume or imbibe the peptide toxin.

The present disclosure also pertains to transgenic mosquitocidal plants producing the targeted fusion peptide. In some preferred embodiments, the plants are nectar plants, but they may be any suitable plants, including trees and shrubs. Preferred nectar plants that may be engineered as transgenic mosquitocidal plants include the common garden impatiens plant, a plant that grows with no required maintenance throughout the moist tropics but is also the top-selling commercial bedding plant worldwide. Studies have shown that impatiens (particularly *Impatiens walleriana*) excels in terms of mosquito attractiveness, nectar protein output and ability to be genetically transformed. In preferred embodiments, an impatiens plant is engineered to express a toxin, solely in nectar, which is nontoxic to honeybees but which effectively controls mosquitoes in outdoor garden trials. These transgenic plants serve as role models for safety, since they are non-crop plants, are specific to one pest species, and can be engineered to have no ability to spread the toxin transgene to the surrounding ecosystem.

In preferred embodiments, an exogenous genetic construct is used to express a targeted toxin peptide for isolation and purification, or to transform a plant into a transgenic mosquitocidal plant. The construct preferably includes different aspects. Plant-specific promoters, such as impatiens nectar promoters, are utilized. An insecticidal toxin peptide is expressed from the construct. A targeting peptide that will form a peptide fusion with the toxin peptide is also expressed, preferably to target mosquitoes by specific binding, such as binding to the gut epithelium. The targeted toxins are toxic to mosquitoes but not to nontarget insect species. These features accomplish the mosquitocidal aspects of the toxin peptide. The mosquitocidal nectar plants are inexpensive, highly scalable, ecologically safe, and require little or no maintenance. This technology is capable of providing mosquito control over very large areas for decades at a time.

BRIEF DESCRIPTION OF DRAWINGS

FIG. 6 shows a comparison of *Aedes aegypti* survival curves after oral administration of targeted and untargeted toxins.

FIG. 8 shows a comparison of *Culex quinquefasciatus* survival curves after oral administration of *Aedes*-targeted toxins and untargeted toxins.

DETAILED DESCRIPTION OF PREFERRED EMBODIMENTS

Figure 1:
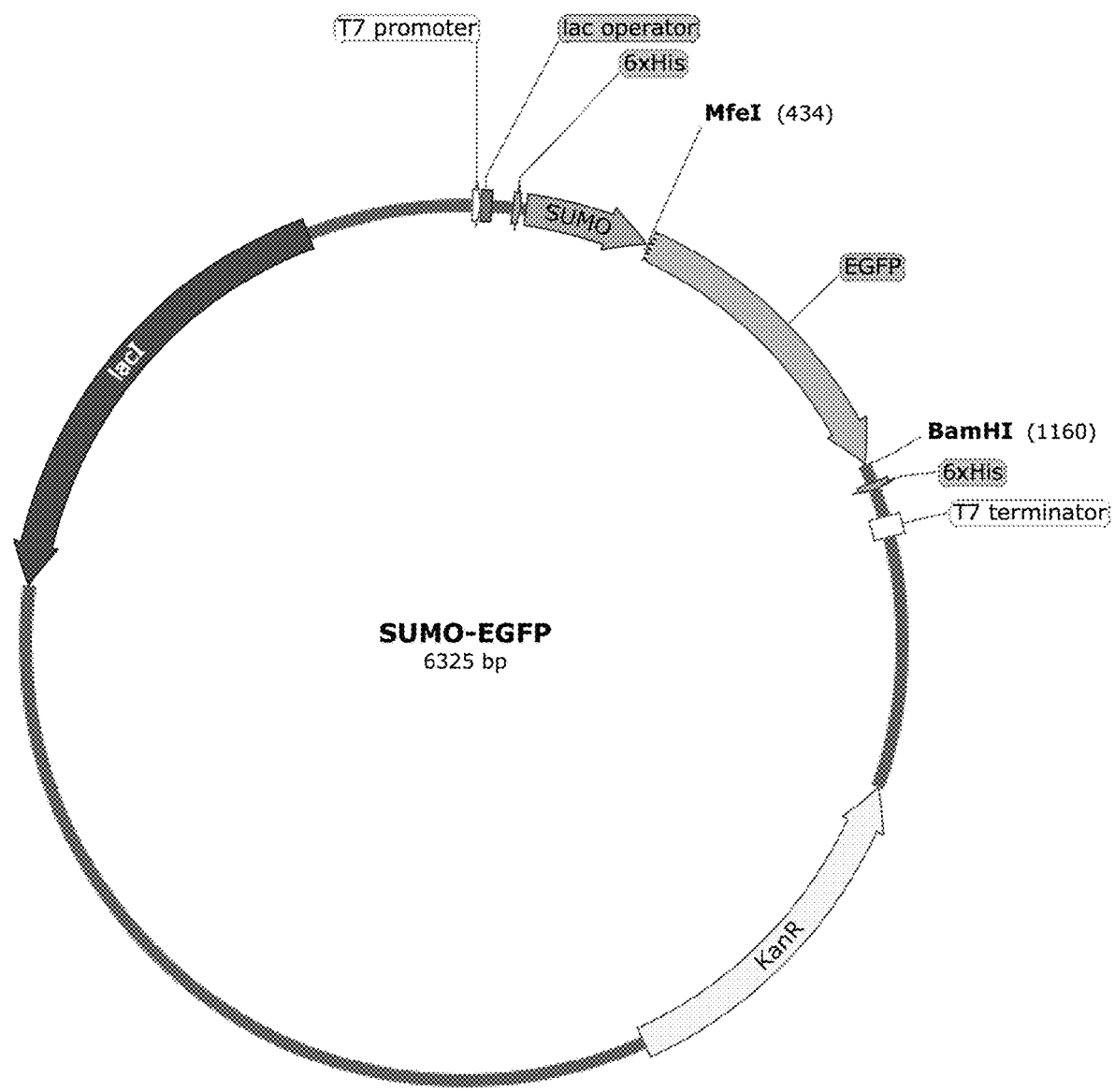
FIG. 1 shows a construct for *E. coli* expression of untargeted enhanced green fluorescent protein (EGFP).

The present disclosure relates to targeted toxin peptides that are toxic to mosquitoes and not to other non-target species. The present disclosure also relates to mosquitocidal plants that express exogenous genes encoding toxins specific to mosquitoes.

In preferred embodiments, the present technology pertains to toxins targeted to mosquitoes. The toxins are fused toxin peptides made up of a targeting domain fused to a toxin domain. The targeting peptide generates a specific association with mosquitoes, such as by causing the fused toxin peptide to bind mosquitoes in a way that induces toxicity. In preferred embodiments, the targeting peptide specifically targets a genus or species of mosquito. There are three particular species of mosquito that are most implicated in the spread of disease—*Aedes aegypti*, which carries yellow fever, Zika, chikungunya, dengue, and encephalitis, *Anopheles gambiae*, which carries malaria, and various species of the *Culex* genus, which carry West Nile virus, encephalitis, and filariasis. In a preferred embodiment, the targeting peptide is designed to target *Aedes aegypti*. Domain III of the glycoprotein of dengue virus has been shown to be the active structure which allows the dengue virus particle to bind to mosquito gut epidermal cells in order for the virus to successfully enter the cells (Hrobowski (2005) Virology Journal 2:49). In a preferred embodiment, a peptide derived from Domain III of the glycoprotein of dengue virus is used to target insecticidal peptides to the gut of *Aedes aegypti*. Using this targeting protein to direct the fused toxin peptide specifically to the mosquito gut will result in the toxin being lethal to the mosquito without affecting honeybees and other pollinators.

In further preferred embodiments, the targeting peptide has the following sequence: MIGVEPGQLKLNWFKK (SEQ ID NO:1).

In additional preferred embodiments, the targeting domains may be derived from sequences from Domain III of the Zika or West Nile viruses. The targeting domains may be designed to target other species of mosquitoes, such as various species of the *Culex* genus, in addition to *Aedes* mosquitoes. Appropriate targeting domains work similarly to Domain III of the glycoprotein of dengue virus in that they allow the viruses from which they are derived to bind specifically to mosquitoes. Any suitable targeting peptide may be utilized so long as it (1) can be expressed in the plant, (2) facilitates specific binding to a target mosquito in a location that would induce toxicity, such as the gut, and not to any nontarget species, and (3) is capable of forming a fusion peptide with the selected peptide toxin. Dengue, Zika, and West Nile viruses are all flaviviruses and sequences from Domain III of each of these viruses should work effectively as targeting peptides in the current disclosure.

In further preferred embodiments of the mosquitocidal plants, a toxin is selected that is toxic to mosquitoes upon binding to the gut. Notably, it is not necessary to utilize a toxin that demonstrates a complete lack of toxicity to other species of insects. The targeting peptide that is bound to the toxin ensures that the toxin specifically affects mosquitoes only, even if the peptide is imbibed from the impatiens nectar by other insects. In preferred embodiments, the toxin peptide is the Hv1a spider toxin peptide. This toxin peptide has been targeted to aphids successfully.

In further preferred embodiments, the toxin peptide has the following sequence: SPTCIPSGQPCPYNENCCSQSCTFKENENGNTVKRCD (SEQ ID NO:2).

Additional preferred embodiments utilize other toxins in the fusion peptide, including antimicrobial peptides naturally found in nectar, which may be converted to mosquito toxicity. Any suitable toxin peptide may be utilized so long as it (1) can be expressed in the plant, (2) is toxic to mosquitoes, and (3) is capable of forming a fusion peptide with the selected targeting peptide. Examples include the toxin Cry11B or any of the mosquitocidal Cry toxins from *Bacillus thuringiensis*. These are highly toxic to mosquito larvae in particular. Other suitable toxins include laterosporulin (a bacteriocin from *Brevibacillus* bacteria) and *Amblyomma* defensin peptide-2 (a defensin from *Amblyomma hebraeum* tick), which are antimicrobial peptides. Both of these are expressed well in transgenic tobacco plants.

In additional embodiments, the fused toxin peptide is made up of a suitable targeting peptide connected to a suitable toxin peptide through a suitable linker. In additional preferred embodiments, the targeting peptide of SEQ ID NO:1 and the toxin peptide of SEQ ID NO:2 are linked through a linker having the sequence: GGSGGGSGG (SEQ ID NO:3).

Preferred embodiments pertain to the fused toxin peptide itself and to methods of producing the fused toxin peptide, such as by expression in *E. coli* or yeast followed by extraction, isolation, or purification of the peptide into a form that can be used as a mosquitocidal toxin. The fused toxin peptide may be combined with any suitable carrier, such as sugar or a nectar-like substance, to produce a mosquitocidal substance that is likely to be imbibed or consumed by mosquitoes. Due to the targeted specificity of the fused toxin peptide to mosquitoes, the substance will not be toxic to non-target species.

Further preferred embodiments pertain to transgenic mosquitocidal plants engineered to express the fused toxin peptide in a fashion that makes the peptide available to mosquitoes for imbibition or consumption, or otherwise exposes the peptide to mosquitoes for uptake. In some preferred embodiments, the transgenic mosquitocidal plants are nectar plants, due to the strong natural attraction that mosquitoes have for nectar.

Preferred embodiments of mosquitocidal nectar plants utilize the most common species of garden impatiens, *Impatiens walleriana*, a native of East Africa. Impatiens are the most common bedding plant worldwide. They are inexpensive, easy to grow and require little upkeep. A recent ecological study demonstrated that impatiens can grow without maintenance (ferally) throughout the moist tropics and in much of the moist temperate zones as well, closely matching the ranges of *Aedes* and *Anopheles* mosquito vector species. Specifically, the adaptive range of impatiens includes all of the eastern USA, most of Latin America, South East Asia, China, India, Europe and most of Africa. In frost-free areas, it is a permanent planting. In frost zones, it is planted once per year in spring.

Furthermore, *Impatiens walleriana* is highly attractive to mosquitoes and can be engineered genetically without difficulty by those skilled in the art. The genome of *Impatiens walleriana* has been sequenced. The promoter (3 kb of DNA) driving the expression of the most highly expressed nectar protein (a phylloplanin analog) has been assembled and is used in preferred embodiments to drive the expression of mosquito-targeted toxin peptides in *Impatiens walleriana*. Genes corresponding to native impatiens antimicrobial peptides and insecticidal peptides can be isolated from the genomic sequencing. In additional preferred embodiments, these can be targeted to mosquitoes by using genetic insertion cassettes that contain a minimum of foreign DNA, with almost exclusively native impatiens DNA.

The transgenic mosquitocidal plants are uniquely positioned to be a transgenic biosafety role model. This technology has several properties that will facilitate acceptance by the EPA and the public. First, the technology is reversible. Unlike gene drive proposals, it will always be possible to reverse mosquito control by uprooting the plants. Impatiens, as an example, produce no persistent rhizomes or tubers. Also, the technology is local and predictable. Control areas are determined by where humans plant the plants. In addition, some preferred plants, such as impatiens, can be commercially produced via cuttings or seeds. Thus, seed and pollen toxin gene excision technology (to prevent transgene escape to the ecosystem) will not interfere with commercial production. Also, no toxic effects on nontarget honeybees or other nontarget insects are expected. This is also a medical application, not a food product. Unlike GMO crops, the plants will not become part of the human food chain. This application is also purchased and installed by the end-user. Unlike food products produced at distant farms, this solution is end-user ownership of the technology, which fosters acceptance. Finally, garden plants in particular are a traditional and established part of residential life. The present technology makes mosquito control "part of the landscape."

Accordingly, preferred embodiments of the present disclosure include a method for producing a modified plant expressing mosquitocidal toxins, including mosquitocidal nectar plant expressing mosquitocidal toxins in nectar of the plant. The method includes inducing expression of an exogenous gene construct that encodes a fused toxin peptide in cells of the plant, such that the fused toxin peptide is actually present and expressed innately by the plant. The fused toxin peptide includes a mosquito targeting peptide fused to a toxin peptide and is specifically toxic to mosquitoes. In additional preferred embodiments, the plant is *Impatiens walleriana*. In further preferred embodiments, the mosquito targeting peptide targets one or more of *Aedes, Anopheles*, or *Culex* mosquitoes. In additional preferred embodiments, the mosquito targeting peptide targets *Aedes aegypti* mosquitoes, such as by binding to gut epithelium of *Aedes aegypti* mosquitoes. In additional preferred embodiments, the toxin peptide is a peptide having toxicity against mosquitoes and may preferably be a Hv1a spider toxin peptide. In further preferred embodiments, the fused toxin peptide lacks toxicity against other organisms.

Preferred embodiments of the present disclosure utilize an exogenous gene construct that includes a promoter specific to the plant, a gene encoding the mosquito targeting peptide, and a gene encoding the toxin peptide. In additional preferred embodiments, expression of the exogenous gene construct is induced in the plant by transforming at least one nectar-producing cell of the plant with the exogenous gene construct to produce a modified plant expressing the fused toxin peptide in the nectar of the plant.

Additional preferred embodiments relate to producing modified plants that will not express the toxin in tissues other than nectar. In these preferred embodiments, expression of a terminator cassette is also induced in the modified plant, and the terminator cassette excises the exogenous gene construct from nucleic acid found in cells of the plant other than cells producing nectar, such as seeds, pollen, roots, and leaves. Thus, the modified plant expresses the fused toxin peptide in its nectar and fails to express the fused toxin peptide in non-nectar tissues.

Further preferred embodiments of the present disclosure include a modified mosquitocidal plant, wherein the modified plant expresses an exogenous gene construct encoding a fused toxin peptide in cells of the plant in a manner that makes the fused toxin peptide available for mosquito consumption, exposure, or general uptake, wherein the fused toxin peptide comprises a mosquito targeting peptide fused to a toxin peptide, and wherein the fused toxin peptide is toxic to mosquitoes. In further preferred embodiments, the plant is a nectar-producing plant and the fused toxin peptide is expressed in nectar of the plant. In further preferred embodiments, the modified plant is *Impatiens walleriana*. Additional preferred embodiments of the modified plant express a mosquito targeting peptide as part of the fused toxin peptide that targets *Aedes, Anopheles*, or *Culex* mosquitoes, or preferably one that targets *Aedes aegypti* mosquitoes. The mosquito targeting peptide may preferably binds to gut epithelium of *Aedes aegypti* mosquitoes. Generally, in preferred embodiments, the toxin peptide is a peptide having toxicity against mosquitoes, and preferably the toxin peptide is a Hv1a spider toxin peptide. In additional preferred embodiments, the fused toxin peptide expressed by the modified mosquitocidal plant lacks toxicity against other organisms.

Additional preferred embodiments include a seed of the modified mosquitocidal plant.

Further preferred embodiments of the present disclosure include a modified mosquitocidal *Impatiens walleriana* plant, wherein the modified plant expresses (a) an exogenous gene construct encoding a fused toxin peptide in cells of the plant producing nectar, wherein the fused toxin peptide comprises a mosquito targeting peptide fused to a toxin peptide, wherein the mosquito targeting peptide binds to gut epithelium of *Aedes aegypti* mosquitoes, wherein the toxin peptide is a Hv1a spider toxin peptide, and (b) a terminator cassette, wherein the terminator cassette excises the exogenous gene construct from nucleic acid found in cells of the plant other than cells producing nectar, and wherein the modified plant fails to express the fused toxin peptide in non-nectar tissues of the modified plant.

Example 1

In a previous study, 37 species of plants were surveyed for mosquito attractiveness, nectar protein output and the ability to be genetically transformed. Among these candidates, the common garden impatiens plant (*Impatiens walleriana*) excelled in all areas (Chen and Kearney, Acta Tropica (2015) 146:1-88). Since then, the proteome and transcriptome of nectar and nectary organs were examined and the major protein produced in nectar was identified. The corresponding gene from the impatiens genome was cloned, and the corresponding promoter to be used to express a peptide toxin in nectar was identified. *Arabidopsis* nectary promoters were also used to create transgenic impatiens plants expressing a marker gene in nectar. The GUS marker gene was expressed in impatiens using *Arabidopsis* nectary-specific promoters, demonstrating that these plants can serve as nectar delivery vehicles for foreign proteins. The nectar transcriptome, and leaf and stem control transcriptomes, from impatiens have been analyzed.

Sequencing and analysis of the *Impatiens walleriana* genome facilitates the isolation of impatiens nectar promoters. RNA-Seq data from nectaries, stem and leaf tissue have been obtained, as well as mass spectrometry data from nectar proteins. The promoters of highly expressed nectar proteins are identified and cloned. These promoters are assayed for nectar expression of RFP fluorescent marker in transgenic impatiens.

Different targeting peptides are tested for simple binding to mosquito gut epithelium, including *Aedes aegypti* gut epithelium. An identified target peptide is a peptide derived from Domain III of the glycoprotein of dengue virus. Targeting peptide/eGFP fusions are produced in *E. coli* and the fusion proteins suspended in 5% sucrose for imbibition. After feeding, mosquito guts are examined by fluorescence microscopy. The targeting peptide sequences are lengthened or shortened to optimize binding. The best binding targeting peptides are used to produce targeting peptide/insecticidal peptide fusions, including targeting peptide/Hv1a insecticidal peptide fusions. These fusion peptides are expressed in *E. coli*, purified, and fed to mosquitoes to determine *Aedes aegypti* mortality. A similar test is conducted on a nontarget organism such as fruit flies to demonstrate lack of nontarget toxicity.

Transgenic plants expressing targeted fusion peptides have been shown to be specifically resistant to *Fusarium* root rot fungus and aphids. In Bonning et al. (2014) Nature Biotechnology 32(1):102, the Hv1a spider toxin peptide was fused to the coat protein of a plant luteovirus. This virus naturally binds itself to the stylet of aphids via its coat protein, hitching rides inside the aphid from plant to plant. The Hv1a peptide is not toxic to the aphids by imbibition, but, when fused to the luteovirus coat protein, it is very toxic, and specific only to aphids, not other insects.

The strongest nectar promoter is used to test a variety of insecticidal peptides for expression potential in impatiens nectar. Genes fusing the best gut-targeting and insecticidal sequences are expressed in *E. coli* and tested against mosquitoes by imbibition. The best fusion construct is put into impatiens. The resulting plantlets are multiplied, to build up stock for field trials, from the multiple bud clusters prolifically produced in impatiens tissue culture. Nontarget morality assays are conducted, including those for honeybees, lacewing, ladybird beetles and one butterfly species, to demonstrate lack of nontarget toxicity.

Field tests are conducted using outdoor mesocosm experiments. Mixed-species test gardens, containing several mosquitocidal nectar impatiens mixed with competing garden plants, are configured inside an 8'×10' mesh cage at residential locations. Mosquitoes are introduced and mortality recorded.

Example 2

This example demonstrates targeting of *Aedes aegypti* mosquitoes by using a peptide from the Domain III sequence of the dengue virus glycoprotein. This sequence allows dengue virus to bind to mosquito gut linings and begin the infection process of the mosquito. The active portion of this glycoprotein was fused to EGFP fluorescent protein and the fusion protein (including the stabilization protein, SUMO) was expressed in *E. coli*. The purified protein was then added to 10% sucrose and fed to mosquitoes in a pulse-chase manner to ensure that any fluorescence observed in the gut was truly due to stable binding to the gut lining.

The pE-SUMOstar vector from LifeSensors (Malvern, Pa.) was used for *Escherichia coli* expression in the competent *E. coli* strains BL21(DE3) and 10-beta from NEB (New England Biolabs, Ipswich, Mass.). gBlocks codon-optimized for *E. coli* expression containing EGFP, a Dengue/EGFP fusion, the toxin Hv1a, and a Dengue/Hv1a fusion sequences were obtained from IDT (Skokie, Ill.). All *Aedes aegypti* mosquito eggs and *Culex quinquefasciatus* larvae were obtained from Benzon Research Inc. (Carlisle, Pa.).

Figure 2:
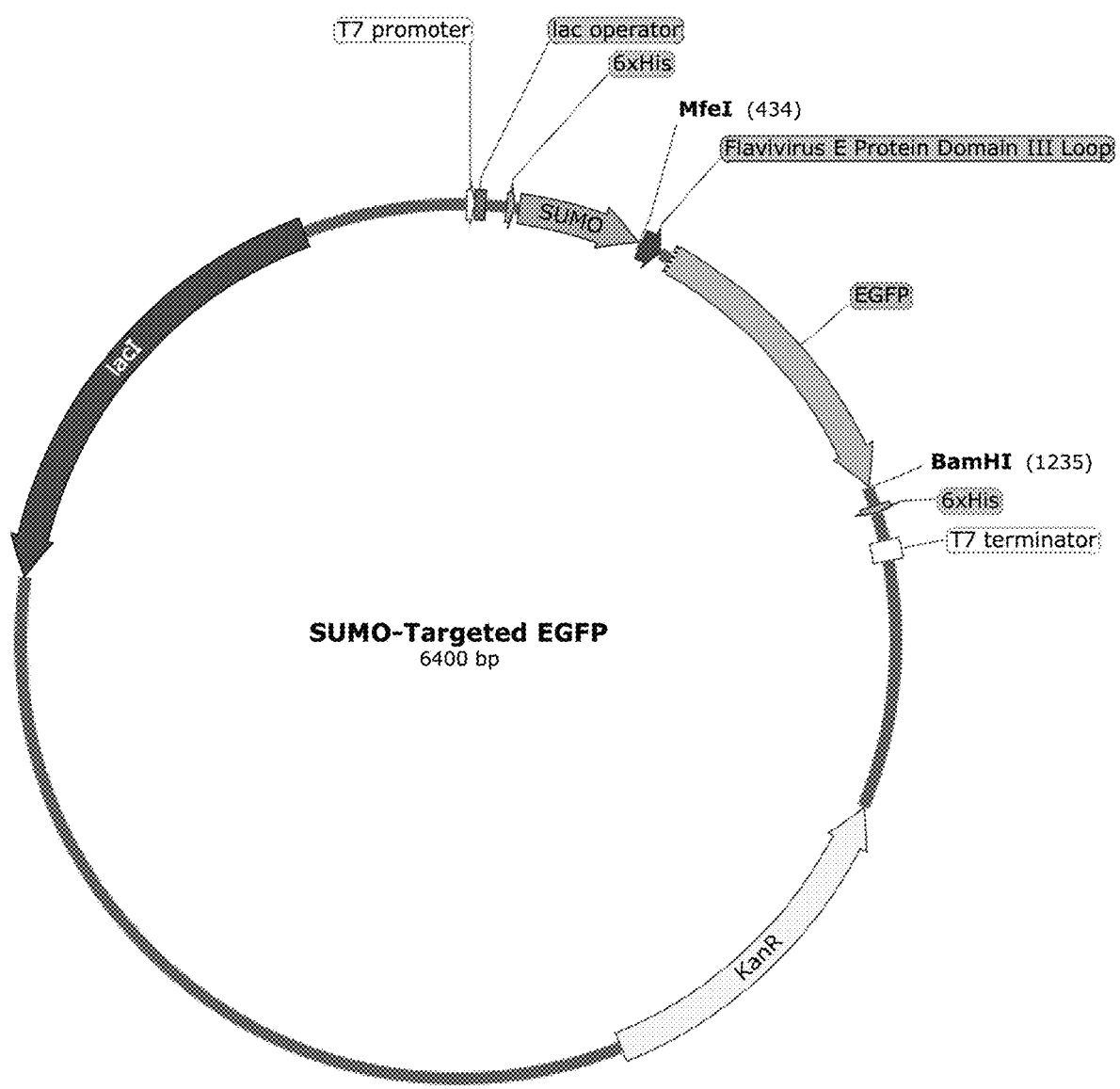
FIG. 2 shows a construct for *E. coli* expression of *Aedes*-targeted EGFP.

Two otherwise identical constructs were built to express the following in *E. coli*:
 1. EGFP marker
 2. Targeted EGFP marker Each of these constructs was a SUMO vector containing the SUMO stabilization protein fused to the payload peptide, as shown in FIG. 1 and FIG. 2. Expression was controlled by the lac operator, T7 promoter, and T7 terminator. The 6×His tags were made available for downstream purification. KanR and lacI were included for clonal selection. Flavivirus E protein Domain III loop (SEQ ID NO:1) was used for targeting the fusion protein to *Aedes aegypti* gut linings EGFP was the fluorescent marker protein gene. SUMO vectors are commercially available, and EGFP is a standard marker protein.

gBlocks were constructed for EGFP, a Dengue/EGFP fusion, the toxin Hv1a, and a Dengue/Hv1a fusion sequences. The Dengue targeting domain was taken from the last 45 bp of the E glycoprotein Domain III from the Dengue virus. The synthesized gBlock sequences were amplified with sequence-specific primers designed to flank the sequences with the restriction enzyme sites for MfeI and BamHI, respectively, using the NEB Q5® High-Fidelity DNA Polymerase (NEB, PCR Using . . . (2018)). These PCR-amplified products were run on a 1% agarose gel and were gel-purified with the Promega Wizard® SV Gel and PCR Clean-Up System (Promega, Madison, Wis. (2018)). The purified PCR products and pE-SUMOstar vector were digested with the restriction enzymes MfeI and BamHI for 1 hr at 37° C. These digested products were then run on a 1% agarose gel and were gel-purified with the Promega Wizard® SV Gel and PCR Clean-Up System. The digested PCR products were ligated into the digested pE-SUMOstar vector using the NEB T4 DNA ligase (NEB, Ligation Protocol . . . (2018)). These recombinant plasmids were electroporated into NEB 10-beta Competent *E. coli* and the transformed colonies were then selectively grown out overnight at 37° C. on agar plates containing LB and 50 µg/ml kanamyacin. Positively-transformed colonies were confirmed with the previously mentioned primers using the NEB Taq polymerase, inoculated into 10 ml of LB containing 50 ug/ml kanamycin, and grown out overnight on a 37 C shaker (NEB, PCR Protocol . . . (2018)). The positive recombinant plasmids were purified from the LB cultures using the Promega Wizard® Plus SV Minipreps DNA Purification System and were transformed into chemically-competent NEB BL21 *E. coli* (Promega, Wizard® Plus . . . (2018)).

Positive BL21 transformants were grown out overnight on a 37° C. shaker in 20 ml of 2×YT broth containing 50 ug/ml kanamycin. Secondary cultures of 500 ml 2×YT containing 50 ug/ml kanamycin were inoculated with the 20 ml primary cultures and shaken (220 rpm) at 37° C. to an OD600 of 0.7. Protein expression was induced in the cultures with 0.1 mM IPTG and overnight shaking (180 rpm) at 14° C. The cells were harvested with centrifugation at 8,000×g for 1 hr at 4° C. The cells were resuspended in 1×PBS and lysed overnight at −20° C. with 0.1 mg/ml lysozyme. The lysed suspensions were thawed and sonicated with a probe sonicator at 40% amplitude. The sonicated slurry was centrifuged at 80,000×g for 1 hr at 4° C. The supernatant was collected and purified with nickel column chromatography using 1×PBS as the binding and wash buffer and 1×PBS containing 500 mM imidazole as the elution buffer. The purified proteins were dialyzed overnight at 4° C. in 1×PBS to remove the imidazole. The purified proteins were run on an 18% SDS-PAGE gel along with 1 mg/ml, 0.5 mg/ml, 0.25 mg/ml, 0.1 mg/ml, and 0.05 mg/ml BSA to confirm their presences and determine their concentrations using ImageJ (Schneider (2012)).

*Ae. aegypti* eggs were raised in plastic trays containing 1 L of tap water and minced fish food (Tetramin®, Tetra, Blacksburg, Va.). *C. quinquefasciatus* larvae were transferred to plastic trays upon arrival and given the minced fish food supplemented with liver powder. All colonies were maintained at 27±1° C., 70±5% RH. Once the mosquitoes reached their pupae stage, they were transferred to plastic tubes to aid in sex identification upon adulthood.

Each EGFP peptide was used to make a 10% sucrose solution. A buffer negative control was made using 1×PBS to make a 10% sucrose solution. Each fluorescent protein and control sucrose solution was added to a cotton ball inside of a 4 ml container and each container was placed into a separate, clear mosquito-assay chamber. 10 male and 10 female *Ae. aegypti* and *C. quinquefasciatus* adult mosquitoes were transferred to each chamber and stored at 27±1° C., 70±5% RH. After 2 days, the mosquitoes were transferred to chambers containing only 10% sucrose. After 2 more days, the midguts were harvested. Fluorescence was visualized under a Stereomicroscope SZX16 with fluorescence unit and a GFP-filter (excitation: 460-495 nm, emission: 510 nm+). All pulse-chase experiments were performed as three separate replicates.

Figure 3:
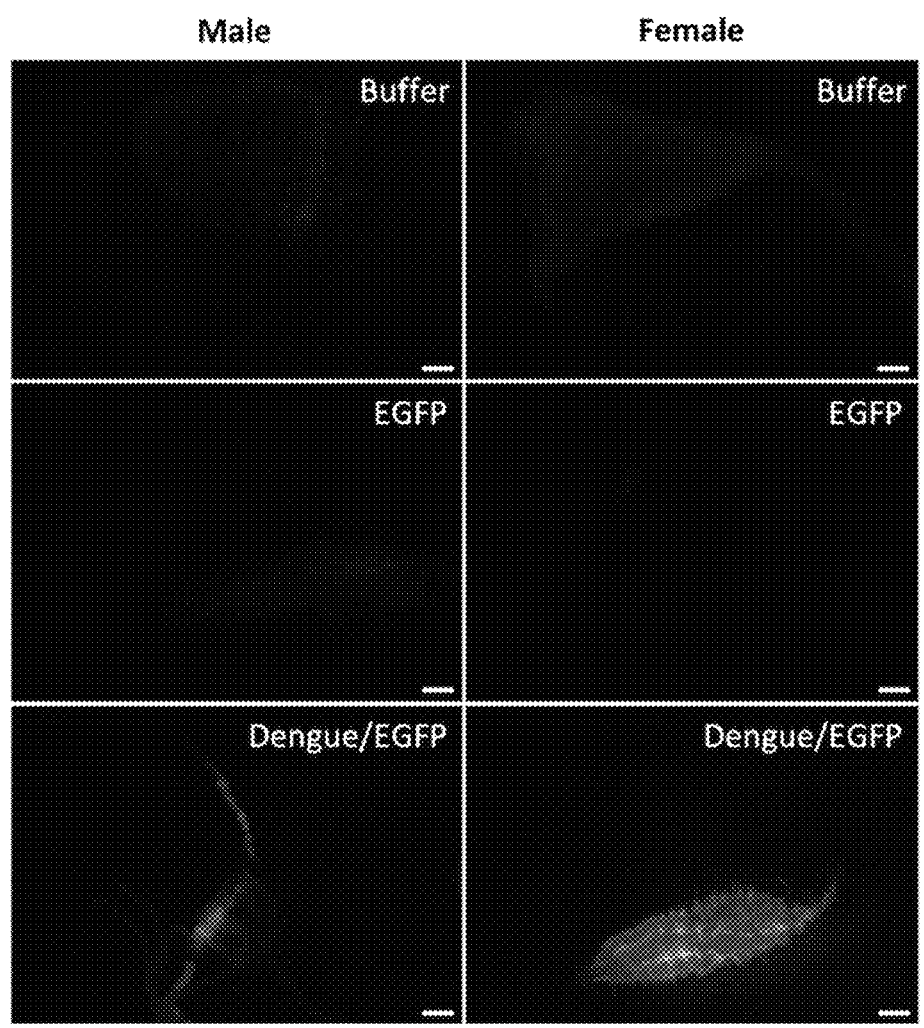
FIG. 3 shows results of a fluorescence assay in *Aedes aegypti* mosquitoes using targeted and untargeted EGFP.

FIG. 3 shows that the EGFP was successfully targeted to the gut linings of *Aedes aegypti*, for both male (left) and female (right) mosquitoes. The bottom panels in FIG. 3 show that dengue peptide-targeted EGFP remained attached to the gut linings after 2 "pulse" days of mosquito feeding off 10% sucrose containing targeted EGFP, followed by 2 "chase" days feeding of 10% sucrose alone. The middle panels in FIG. 3 show that in the negative control experiments, untargeted EGFP did not remain in the gut after the chase with 10% sucrose. In the null control experiment shown in the top panels of FIG. 3, no fluorescence was seen with continual feeding with 10% sucrose suspended in PBS buffer.

Example 3

This example demonstrates use of a host-binding protein from a virus specific to a particular mosquito species to target that mosquito species. The results demonstrate targeted kill of *Aedes aegypti* mosquitoes by using a peptide from the Domain III sequence of the dengue virus glycoprotein. Specifically, the weak native toxicity of Hv1a insecticidal toxin against *Aedes aegypti* was greatly enhanced by fusing it to the dengue-derived targeting peptide.

Figure 4:
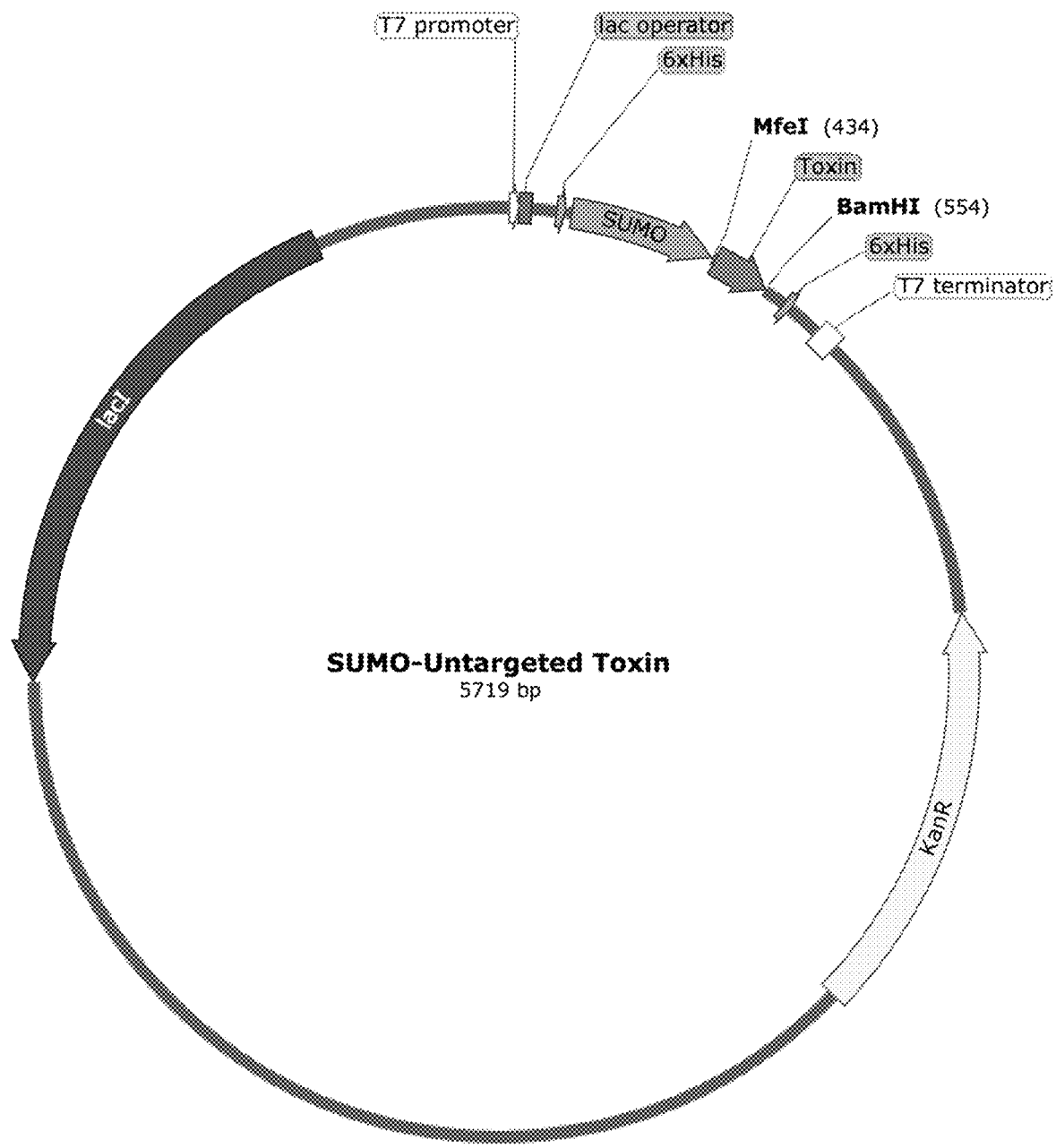
FIG. 4 shows a construct for *E. coli* expression of untargeted Hv1a insecticidal toxin.
Figure 5:
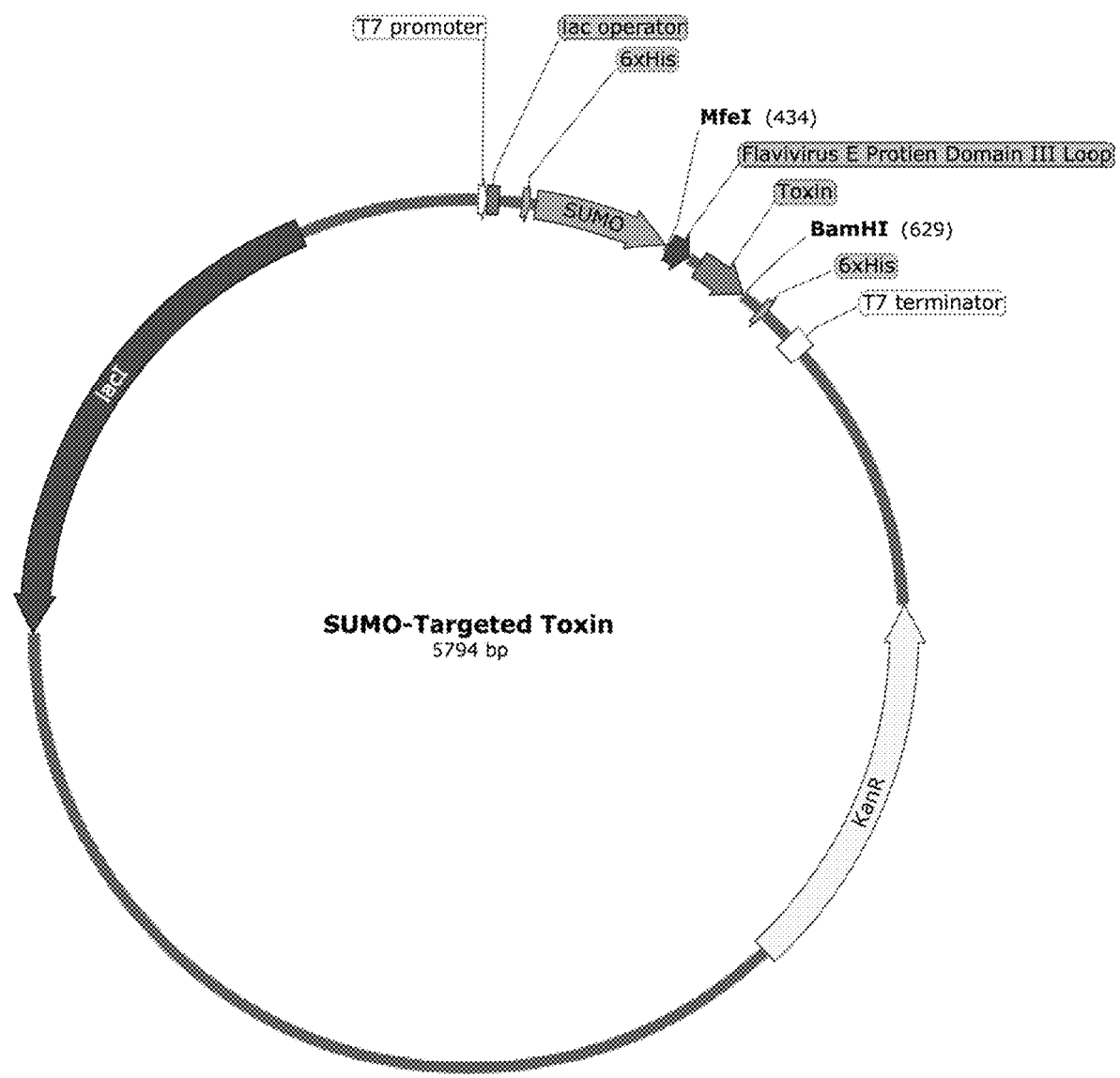
FIG. 5 shows a construct for *E. coli* expression of *Aedes*-targeted Hv1a insecticidal toxin.

In this example, two constructs, otherwise identical to the previous two constructs used in Example 2, were built to express the following in *E. coli*:
1. Hv1a toxin
2. Targeted Hv1a toxin Each of these constructs, shown in FIG. 4 and FIG. 5, was a SUMO vector containing the SUMO stabilization protein fused to the payload peptide. Expression was controlled by the lac operator, T7 promoter, and T7 terminator. The 6×His tags were made available for downstream purification. KanR and lacI were present for clonal selection. Flavivirus E protein Domain III loop (SEQ ID NO:1) was included for targeting the fusion protein to *Aedes aegypti* gut linings "Toxin" refers to the Hv1a toxin gene (SEQ ID NO:2).

Each toxin was diluted to 500 ug/ml and used to make a 10% sucrose solution. 1×PBS was used again to make a buffer negative control 10% sucrose solution. Each toxin and control sucrose solution was added to a mosquito-assay chamber as described above. 10 male and 10 female *Ae. aegypti* and *C. quinquefasciatus* adult mosquitoes were transferred to each chamber and stored at 27±1° C., 70±5% RH. Mosquitoes were allowed to imbibe 10% sucrose containing the Hv1a toxin, the Hv1a toxin fused to the dengue-derived peptide which targets *Aedes*, or no added protein ("buffer"). Death events were recorded every 24 h for 3 days. 3 replicates were conducted for this experiment. GraphPad Prism 7 was used to analyze the recorded data for significance using the Log-rank (Mantel-Cox) test and to represent the data in a survival curve with 95% confidence intervals (CI).

Figure 6:
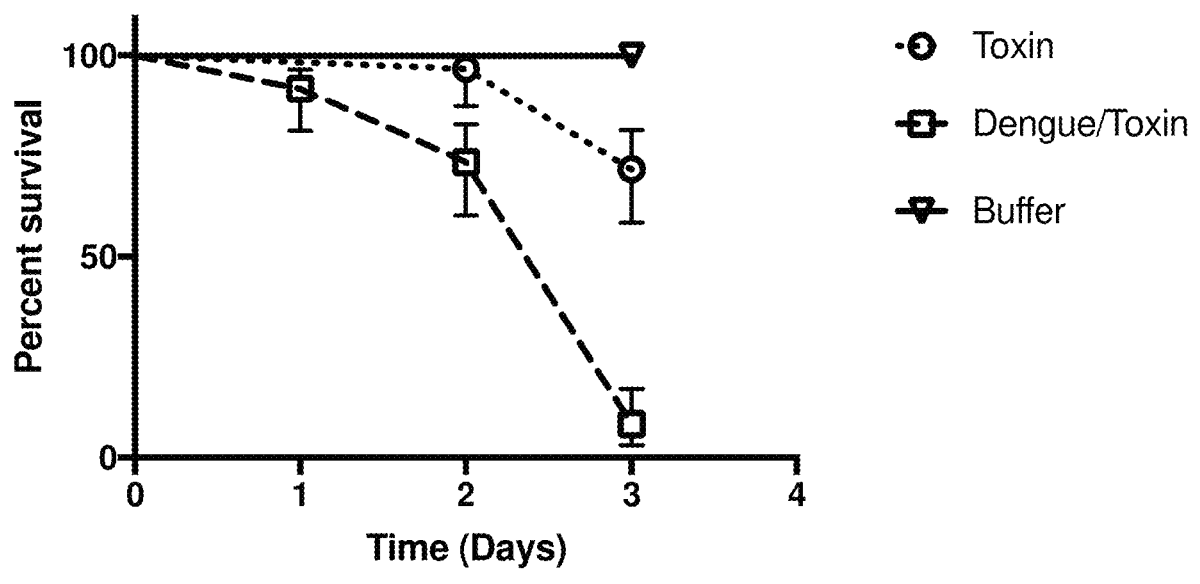

Results of the targeted toxin experiment against *Ae. aegypti* target mosquitoes are shown in FIG. 6. No mosquitoes died which fed on 10% sucrose alone ("buffer"), and a slight amount of toxicity was observed in mosquito populations fed with 10% sucrose containing toxin alone. In contrast, a greatly enhanced toxicity was recorded with *Aedes*-targeted toxin containing the targeting peptide from dengue virus. Bars indicate 95% confidence limits.

Example 4

This example demonstrates the extreme specificity of the targeting mechanism described herein. Results show that the targeted toxin has no greater toxicity than the nontargeted toxin when imbibed by the mosquito *Culex quinquefasciatus*, which is not a host for dengue virus. In other words, the minimal toxicity of the base toxin is not enhanced by the targeting peptide.

Figure 7:
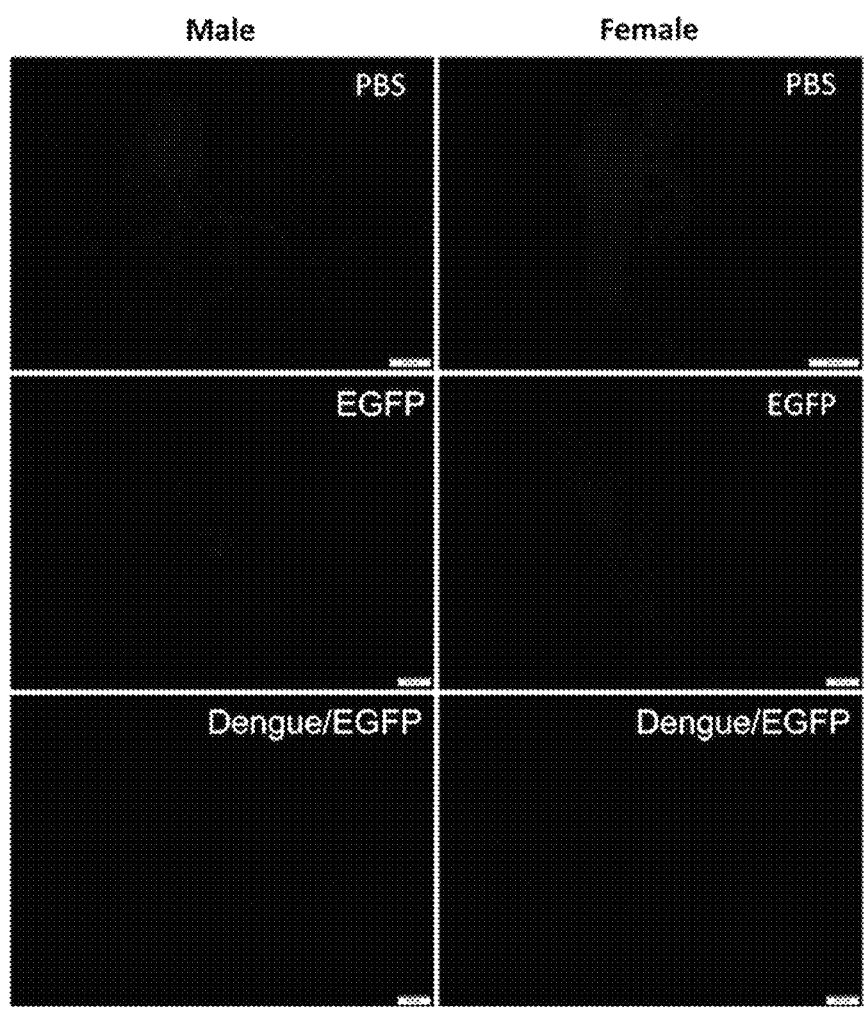
FIG. 7 shows results of a fluorescence assay in *Culex quinquefasciatus* mosquitoes using EGFP targeted to *Aedes* mosquitoes and untargeted EGFP.

As described in Example 3, the same constructs were used and *C. quinquefasciatus* adult mosquitoes were also allowed to imbibe 10% sucrose containing the Hv1a toxin, the Hv1a toxin fused to the dengue-derived peptide which targets *Aedes*, or no added protein ("Buffer"). Results of the fluorescence study are shown in FIG. 7. *Aedes*-targeted EGFP did not bind to the gut linings of *Culex quinquefasciatus*, for either male or female mosquitoes. The bottom panels of FIG. 7 show that dengue peptide-targeted EGFP was not seen in the gut linings after 2 "pulse" days of feeding off 10% sucrose containing targeted EGFP followed by 2 "chase" days feeding off 10% sucrose alone. The middle panels in FIG. 7 show that in the negative control experiments, untargeted EGFP did not remain in the gut after the chase with 10% sucrose. The top panels of FIG. 7 show that in the null control experiment, no fluorescence was seen with continual feeding with 10% sucrose suspended in PBS buffer.

Figure 8:
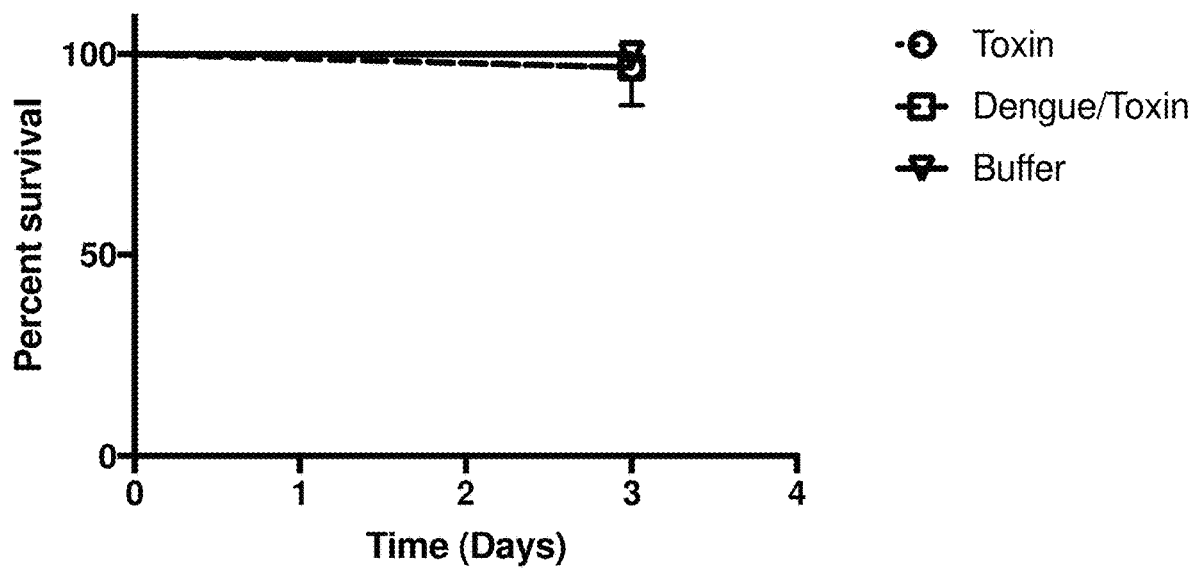

FIG. 8 shows the results in terms of percent survival of the *Culex quinquefasciatus* nontarget mosquitoes fed with *Aedes*-targeted insecticidal peptide. Mortality counts were conducted daily. There was no significant difference between mosquitoes fed on 10% sucrose alone ("Buffer"), 10% sucrose containing toxin ("Toxin"), or *Aedes*-targeted toxin containing the targeting peptide from dengue virus ("Dengue/Toxin"). Bars indicate 95% confidence limits.

This demonstrates that the targeting mechanism is extremely specific, even to the genus level. The critical test of nontoxicity to bees and other unrelated pollinators is expected to produce the same results, as this more stringent test demonstrates specificity even between different types of mosquitoes.

REFERENCES

The following publications are hereby incorporated by reference.

Bonning et al. (2014) Nature Biotechnology 32(1):102
Hrobowski (2005) Virology Journal 2:49
Chen & Kearney, Acta Tropica (2015) 146:1-88
NEB. PCR Using Q5® High-Fidelity DNA Polymerase (M0491). NEB (2018).
Promega. Wizard® SV Gel and PCR Clean-Up System. Promega (2018).
NEB. Ligation Protocol with T4 DNA Ligase (M0202). NEB (2018).
NEB. PCR Protocol for Taq DNA Polymerase with Standard Taq Buffer (M0273). NEB (2018).
Promega. Wizard® Plus SV Minipreps DNA Purification System. Promega (2018).
Schneider, C. A., Rasband, W. S. & Eliceiri, K. W. NIH Image to ImageJ: 25 years of image analysis. Nat. Methods 9, 671-675 (2012).

What is claimed is:

1. A mosquitocidal toxin, comprising:
a fused toxin peptide, wherein the fused toxin peptide comprises a mosquito targeting peptide fused to a toxin peptide, wherein the toxin peptide is a Hv1a spider toxin peptide, wherein the mosquito targeting peptide is a peptide consisting of SEQ ID NO:1 from Domain III of the glycoprotein of dengue virus, wherein the mosquito targeting peptide targets *Aedes aegypti* mosquitoes, and wherein the fused toxin peptide is toxic to *Aedes aegypti* mosquitoes.

2. The mosquitocidal toxin of claim 1, further comprising a carrier.

3. A method for producing a modified plant expressing mosquitocidal toxins, comprising:
   expressing a nucleic acid construct encoding the mosquitocidal toxin of claim 1 in target cells of the plant; and
   producing a modified plant expressing the fused toxin peptide.

4. The method of claim 3, wherein the plant is a nectar plant, the target cells of the plant are nectar-producing cells, and the modified plant expresses the fused toxin peptide in nectar of the plant.

5. The method of claim 4, wherein the plant is *Impatiens walleriana*.

6. A method for producing a modified plant expressing mosquitocidal toxins in nectar of the plant, comprising:
   expressing a nucleic acid construct encoding the mosquitocidal toxin of claim 1 in cells of the plant producing nectar, wherein the plant is *Impatiens walleriana*; and
   producing a modified plant expressing the fused toxin peptide in the nectar of the modified plant.

7. A modified mosquitocidal plant, wherein the modified plant expresses the mosquitocidal toxin of claim 1 in cells of the plant.

8. The modified mosquitocidal plant of claim 7, wherein the plant is a nectar plant and the modified mosquitocidal plant expresses the mosquitocidal toxin in nectar of the plant.

9. The modified mosquitocidal plant of claim 8, wherein the plant is *Impatiens walleriana*.

10. A seed of the modified mosquitocidal plant of claim 7, wherein the seed comprises the mosquitocidal toxin.

11. The mosquitocidal toxin of claim 1, wherein the toxin peptide comprises SEQ ID NO:2.

\* \* \* \* \*